United States Patent
Greiner et al.

(10) Patent No.: US 10,750,129 B2
(45) Date of Patent: Aug. 18, 2020

(54) HOSPITAL VIDEO SURVEILLANCE SYSTEM

(71) Applicant: KONINKLIJKE PHILIPS N.V., Eindhoven (NL)

(72) Inventors: Harald Greiner, Nufringen (DE); Ihor Olehovych Kirenko, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/325,201

(22) PCT Filed: Aug. 23, 2017

(86) PCT No.: PCT/EP2017/071227
§ 371 (c)(1),
(2) Date: Feb. 13, 2019

(87) PCT Pub. No.: WO2018/037041
PCT Pub. Date: Mar. 1, 2018

(65) Prior Publication Data
US 2019/0199970 A1 Jun. 27, 2019

(30) Foreign Application Priority Data
Aug. 23, 2016 (EP) .................................... 16185306

(51) Int. Cl.
*H04N 7/18* (2006.01)
*G16H 40/67* (2018.01)
(Continued)

(52) U.S. Cl.
CPC ........... *H04N 7/181* (2013.01); *A61B 5/0013* (2013.01); *A61B 5/0077* (2013.01);
(Continued)

(58) Field of Classification Search
CPC ... G06F 19/3418; A61B 5/002; A61B 5/0022; A61B 5/0024; A61B 5/02; A61B 5/743;
(Continued)

(56) References Cited

U.S. PATENT DOCUMENTS 6,057,758 A * 5/2000 Dempsey ................. A61N 1/08
340/539.12
7,477,285 B1 * 1/2009 Johnson ........... G08B 13/19602
348/143
(Continued)

FOREIGN PATENT DOCUMENTS

CN 103284690 9/2013
JP 2002236759 A * 8/2002
(Continued)

OTHER PUBLICATIONS

Machine generated translation of JP2002236759A to Ota et al, Aug. 2002 (Year: 2002).*

*Primary Examiner* — David E Harvey (57) ABSTRACT

The invention relates to a hospital video surveillance system comprising several cameras (2, 3, 4) for acquiring video data for surveilling several patient regions (5, 6, 7). The video data are transmitted from the cameras to a display device and are used to determine physiological properties of patients, wherein the physiological properties are vital signs. The bandwidths for the transmission of the video data are allocated depending on the determined physiological properties. Thus, the bandwidth allocation considers the physiological states of the patients, which can ensure that a sufficient bandwidth is provided where it is really required. This is especially useful, if the overall bandwidth is limited. Moreover, since the video data are used for fulfilling several functions, i.e. surveilling the several patient regions and
(Continued)

determining the physiological properties, the overall system can be very compact and less or no additional physiological sensors might be required.

15 Claims, 6 Drawing Sheets

(51) Int. Cl.
| | |
|---|---|
| A61B 5/11 | (2006.01) |
| A61B 5/00 | (2006.01) |
| A61B 5/0205 | (2006.01) |
| G06K 9/00 | (2006.01) |
| G16H 40/20 | (2018.01) |
| A61B 5/024 | (2006.01) |
| A61B 5/08 | (2006.01) |
| A61B 5/1455 | (2006.01) |

(52) U.S. Cl.
CPC ........ *A61B 5/02055* (2013.01); *A61B 5/1115* (2013.01); *A61B 5/1117* (2013.01); *A61B 5/1128* (2013.01); *A61B 5/742* (2013.01); *G06K 9/00362* (2013.01); *G06K 9/00718* (2013.01); *G06K 9/00771* (2013.01); *G16H 40/67* (2018.01); *A61B 5/02427* (2013.01); *A61B 5/0816* (2013.01); *A61B 5/14552* (2013.01); *G16H 40/20* (2018.01)

(58) Field of Classification Search
CPC ....... A61B 5/746; A61B 5/742; A61B 5/0077; A61B 5/1128; A61B 5/1116; A61B 5/1117; A61B 5/02055; A61B 5/013; G16H 40/67; H04N 7/18; H04N 7/181
See application file for complete search history.

(56) References Cited

U.S. PATENT DOCUMENTS

| | | | |
|---|---|---|---|
| 8,666,116 B2 | 3/2014 | Kirenko | |
| 9,025,826 B2 | 5/2015 | Kirenko | |
| 9,339,210 B2 | 5/2016 | Kersten | |
| 9,892,311 B2* | 2/2018 | Kusens | G16H 40/63 |
| 10,515,063 B1* | 12/2019 | Burtsev | G06F 16/2246 |
| 2003/0193395 A1 | 10/2003 | Ahiska | |
| 2006/0064324 A1* | 3/2006 | Rosenfeld | G16H 50/20 705/2 |
| 2008/0001735 A1* | 1/2008 | Tran | A61B 7/00 340/539.22 |
| 2008/0249376 A1* | 10/2008 | Zaleski | A61B 5/0006 600/301 |
| 2009/0054735 A1 | 2/2009 | Higgins | |
| 2010/0144336 A1* | 6/2010 | Kuk | H04M 1/72525 455/418 |
| 2010/0234695 A1* | 9/2010 | Morris | A61B 5/0002 600/300 |
| 2012/0133774 A1 | 5/2012 | Sarhan | |
| 2012/0140068 A1* | 6/2012 | Monroe | H04N 7/183 348/143 |
| 2012/0203078 A1* | 8/2012 | Sze | G06F 19/3418 600/301 |
| 2012/0253847 A1* | 10/2012 | Dell'Anno | A61B 5/0022 705/3 |
| 2013/0007872 A1* | 1/2013 | Hariharan | H04H 60/48 726/17 |
| 2013/0267873 A1* | 10/2013 | Fuchs | H04N 7/18 600/595 |
| 2013/0314522 A1 | 11/2013 | Ravid | |
| 2013/0343614 A1* | 12/2013 | Kyal | G06K 9/0057 382/107 |
| 2014/0005506 A1 | 1/2014 | Eglhazzawi | |
| 2014/0168397 A1* | 6/2014 | Greco | H04N 7/181 348/77 |
| 2014/0278463 A1* | 9/2014 | Merry | G16H 40/63 705/2 |
| 2014/0286160 A1* | 9/2014 | Zhang | H04L 67/14 370/230 |
| 2014/0334697 A1 | 11/2014 | Kersten | |
| 2015/0245787 A1* | 9/2015 | Kyal | A61B 5/1128 600/476 |
| 2016/0235312 A1* | 8/2016 | Jeanne | A61B 5/72 |
| 2016/0275776 A1* | 9/2016 | Shen | G06F 19/3481 |
| 2017/0076057 A1* | 3/2017 | Burton | G16H 10/60 |
| 2017/0171732 A1* | 6/2017 | Dao | H04W 76/50 |
| 2017/0238805 A1* | 8/2017 | Addison | A61B 5/0205 |
| 2018/0054476 A1* | 2/2018 | Kyser | A61B 5/0077 |
| 2018/0103859 A1* | 4/2018 | Provenzano | A61B 5/02438 |

FOREIGN PATENT DOCUMENTS

| | | |
|---|---|---|
| WO | 2012/037192 | 3/2012 |
| WO | 2012/146957 | 11/2012 |

* cited by examiner

HOSPITAL VIDEO SURVEILLANCE SYSTEM

CROSS REFERENCE TO RELATED APPLICATIONS

This application is the U.S. National Phase application under 35 U.S.C. § 371 of International Application No. PCT/EP2017/071227 filed Aug. 23, 2017, published as WO 2018/037041 on Mar. 1, 2018, which claims the benefit of European Patent Application Number 16185306.4 filed Aug. 23, 2016. These applications are hereby incorporated by reference herein.

FIELD OF THE INVENTION

The invention relates to a hospital video surveillance system, method and computer program. The invention relates further to a camera for being used in the hospital video surveillance system and a data transmission system controller for being used in a data transmission system of the hospital video surveillance system.

BACKGROUND OF THE INVENTION

A hospital video surveillance system comprises several cameras for surveilling several regions within a hospital, in which patients are located, by acquiring video data showing the several regions. The acquired video data are transmitted to a display device located in a caregivers' room, in order to allow a caregiver to monitor the patients via the video data.

A hospital generally has many patients and a large amount of video data is generated and needs to be transmitted to one or several display devices. For coping with this large amount of video data a high data transmission bandwidth is required, which might not be available such that it is might not be possible to surveil all patients continuously in realtime. This can result in a relatively poor quality of the video surveillance of the patients.

SUMMARY OF THE INVENTION

It is an object of the present invention to provide a hospital video surveillance system, method and computer program which allow for an improved video surveillance of patients. It is a further object of the present invention to provide a camera to be used in the hospital video surveillance system and a data transmission system controller for a data transmission system of the hospital video surveillance system.

In a first aspect of the present invention a hospital video surveillance system is presented, wherein the hospital video surveillance system comprises:
  several cameras for surveilling several regions within a hospital, in which patients are located, by acquiring video data showing the several regions,
  a display device for displaying the video data,
  a data transmission system for transmitting the video data from the cameras to the display device, and
  a physiological property determination unit for determining physiological properties of the patients based on the acquired video data, wherein the physiological properties are vital signs,
  wherein the data transmission system is adapted to allocate bandwidths for the transmission of the video data from the cameras to the display device depending on the determined physiological properties.

Since the bandwidth for the transmission of the video data from the cameras to the display device is allocated depending on the determined physiological properties, the bandwidth allocation can consider the physiological states of the patients. For instance, if a physiological property determined for a patient exceeds a predefined threshold, the bandwidth for the transmission of the video data from the camera surveilling the region, in which this patient is located, to the display device can be increased. Moreover, since the video data, which are acquired for surveilling the several regions, are also used for determining the physiological properties of the patient, the overall system can be very compact, wherein less or no additional physiological sensors might be required, which can simplify the hospital video surveillance.

The display device can comprise one or several displays for showing the video data.

The physiological property determination unit can be adapted to determine for a respective patient one or several vital signs based on the respective acquired video data, in order to determine the physiological properties, i.e. the vital signs, of the patients. The one or several vital signs are preferentially indicative of the status of the respective patient's body vital, especially life-sustaining, functions. The one or several vital signs are preferentially selected from a list consisting of the heart rate, the breathing rate, the blood oxygen saturation and the body temperature of the respective patient. Thus, the physiological property determination unit can be adapted to determine for the respective patient one or several vital signs of the list consisting of the heart rate, the breathing rate, the blood oxygen saturation and the body temperature for determining the physiological properties of the patients. The physiological property determination unit can be adapted to determine for each patient the same one or several vital signs. However, the physiological property determination unit can also be adapted to determine for different patients different vital signs.

In an embodiment the physiological property determination unit and the cameras are separate devices, wherein the hospital surveillance system comprises a wired and/or wireless data transmission connection for transmitting the video data acquired by the cameras to the physiological property determination unit. For transmitting the video data the data transmission system can be used, which is also used for transmitting the video data from the cameras to the display device, or another data transmission system can be used.

In an embodiment in each camera a respective physiological property determination unit can be integrated, wherein the respective physiological property determination unit is regarded as being a physiological property determination subunit and is adapted to determine one or several vital signs of the respective patient based on the video data acquired by the respective camera. The several physiological property determination subunits, which can be used for determining the physiological properties of the different patients, can be regarded as forming the physiological property determination unit for determining the physiological properties of the patients.

The data transmission system can be adapted to allocate the bandwidths for the transmission of the video data depending on a history of the determined physiological properties. For instance, if the history of one or several determined physiological properties of a patient shows that the one or several determined physiological properties are relatively stable, it might be assumed that this will also be the case in the future. The data transmission system may then allocate a lower bandwidth to the respective patient. However, if the history of the determined one or several physiological properties shows that the one or several determined physiological properties were relatively unstable in the past, it may be assumed that this will also be the case in the future and the data transmission system may allocate a larger bandwidth for the transmission of the video data from the camera surveilling the respective patient. This can lead to a further improvement of the hospital video surveillance system.

The hospital video surveillance system can also comprise a person detection unit for detecting, besides the patient, a further person within the respective region, wherein the data transmission system can be adapted to allocate the bandwidths for the transmission of the video data depending on the further person detection. In particular, the person detection unit is adapted to perform the further person detection such that it is determined whether the respective person is a caregiver. If a caregiver is close to the respective patient, it can be assumed that the caregiver takes care of the respective patient such that a video surveillance of the patient is not necessarily required. The data transmission system can therefore be adapted to reduce the bandwidth for the transmission of the video data from the camera surveilling the respective patient, if it has been detected that a caregiver like a nurse or a physician is in the surveilled region in which the patient is present. This allows for a further improvement of the video surveillance of the patients.

For detecting the caregiver, video processing techniques can be used, which can consider that the caregivers wear certain clothes having certain colors like a gown having a white or green color. It is also possible that visual signs are attached to the caregivers, wherein the person detection unit can be adapted to detect these visual signs in the video data, in order to determine whether a caregiver is close to the respective patient. If the person detection unit is adapted to perform the person detection based on the video data, each camera might comprise a respective person detection unit integrated into a casing of the respective camera. However, the person detection unit can also be a separate device being separate from the respective camera. Moreover, the person detection unit can be adapted to perform the person detection without using the video data. For instance, to each caregiver an indication like a radio-frequency identification (RFID) may be attached and the person detection unit can be adapted to detect this indication, in order to determine whether a caregiver is within the respective region.

The hospital video surveillance system can also comprise a medical procedure information providing unit for providing medical procedure information being indicative of the respective medical procedure the respective patient undergoes, wherein the data transmission system can be adapted to allocate the bandwidths for the transmission of the video data depending on the provided medical procedure information. The medical procedure information providing unit is preferentially a storing unit in which the medical procedure information is stored already and from which the medical procedure information can be retrieved for providing the same. The medical procedure information providing unit can also be a receiving unit for receiving the medical procedure information from another unit like a patient data server in which patient data including the medical procedure information are stored. Some medical procedures require a stronger video surveillance than other medical procedures such that allocating the bandwidth for the transmission of the video data depending on the provided medical procedure information can lead to a further improved video surveillance of the patients.

The hospital video surveillance system can also comprise a distance information providing unit for providing distance information being indicative of the respective distance of the respective region to a caregivers' room in the hospital, wherein the data transmission system is adapted to allocate the bandwidths for the transmission of the video data depending on the provided distance information. A caregivers' room is a room which is generally used by the caregivers, for instance, by nurses and/or physicians, if the caregivers are not in a patient's room. If the distance between the patient and this caregivers' room is relatively large, the caregivers need a relatively long time to be at the patient's side, if a patient has a problem. It can therefore be more important to allocate a larger bandwidth for the transmission of video data from a camera for surveilling a region having a larger distance to the caregivers' room than for the transmission of the video data from a camera surveilling a region having a smaller distance to the caregivers' room. Considering the distance information can therefore lead to a further improvement of the hospital video surveillance system. The distance information providing unit is preferentially a storing unit in which the distances between the respective regions and the caregivers' room are stored, wherein the storing unit is adapted to provide the stored distances.

The hospital video surveillance system can also comprise a behavior information providing unit for providing behavior information being indicative of the behavior of the respective patient, wherein the data transmission system is adapted to allocate the bandwidths for the transmission of the video data depending on the provided respective behavior information. The behavior information providing unit is preferentially a behavior determination unit for determining the behavior of the respective patient based on the video data and for providing the determined respective behavior as the behavior information. The behavior determination unit can provide several behavior classes, wherein, in order to determine the behavior of a respective patient, it can determine the behavior class of the respective patient, wherein the data transmission system can be adapted to allocate the bandwidth for the transmission of the video data depending on the determined respective behavior class. For instance, the behavior classes can define different degrees of activity, wherein a lower bandwidth can be allocated for the transmission of video data for surveilling a region occupied by a patient for whom a relatively low activity degree has been determined and a higher bandwidth can be allocated for a transmission of video data from a camera surveilling a region occupied by a patient for whom a larger activity degree has been determined. Also this can lead to an improvement of the video surveilling of the patients. The behavior determination unit can also be adapted to determine the behavior, especially the activity, of the respective patient based on a sensor signal generated by a sensor attached to the patient like an accelerometer-based wearable sensor.

The hospital video surveillance system can also comprise a medical condition information providing unit for providing medical condition information being indicative of the respective medical condition of the respective patient, wherein the data transmission system can be adapted to allocate the bandwidths for the transmission of the video data depending on the provided respective medical condition information. The medical condition information can be provided as one of several predefined medical condition classes, wherein the different medical condition classes can indicate how critical the medical condition of the respective patient is. If the medical condition of the respective patient is more critical, the data transmission system controller can allocate a larger bandwidth for the transmission of the video data from the camera surveilling the region occupied by the patient and, if the medical condition of the respective patient is less critical, the data transmission system controller can allocate a smaller bandwidth for the transmission of the video data from the camera surveilling the region occupied by the patient. This can also lead to an improvement of the video surveillance of the patients.

The medical condition information providing unit is preferentially a storing unit in which the medical condition information is stored and from which the stored medical condition can be provided. The medical condition information providing unit can also be a receiving unit for receiving the medical condition information from a patient data server in which patient data including the medical condition information are stored, wherein in this case the medical condition information providing unit is adapted to provide the received medical condition information.

The hospital video surveillance system can also comprise a fall information providing unit for providing fall information being indicative of the respective fall history and/or of the respective fall risk of the respective patient, wherein the data transmission system can be adapted to allocate the bandwidths for the transmission of the video data depending on the provided respective fall information. If a patient has fallen out of a bed in the past and/or has a high fall risk, it is likely that the patient will fall out of the bed also in the future. The data transmission system can therefore be adapted to allocate a higher bandwidth for the transmission of the video data from a camera surveilling a certain region occupied by a patient, if the fall information for this patient indicates that in the past the patient has fallen out of the bed one time or several times and/or if this patient has a relatively high fall risk. This can also lead to an improvement of the video surveillance of the patients.

The fall information providing unit can be a storing unit in which the fall information, particularly the fall history and/or the fall risk, is stored and from which the fall information can be provided. The fall information providing unit can also be a receiving unit for receiving the fall information from another unit like a patient data server in which patient data including the fall history information and/or the fall risk are stored. The fall information providing unit can also be adapted to determine whether a respective patient has fallen out of a bed based on the video data and then store this information, in order to generate and provide the fall history. Moreover, the fall information providing unit can be adapted to determine the fall risk based on one or several past and/or current physiological properties of the respective patient. For instance, the fall information providing unit can comprise assignments between one or several physiological properties and fall risk scores defining the fall risk, wherein the fall information providing unit can be adapted to determine the fall risk based on the assignments and the past and/or current physiological properties of the respective patient. If the fall risk, particularly the fall risk score, is larger than a fall risk threshold, which might predefined and/or selectable by a user, the fall risk might be regarded as being relatively high and a larger bandwidth might be allocated for the respective patient.

In an embodiment the hospital video surveillance system further comprises physiological property measuring units for determining a measured physiological property of a respective patient based on a measured sensor signal received from a physiological sensor attached to the respective patient, wherein the data transmission system can be adapted to allocate the bandwidths for the transmission of the video data depending on the measured respective physiological property. Thus, in an embodiment not only the video data are used for determining the physiological properties of the patient, but also sensor signals received from physiological sensors attached to the patients. These physiological sensors can be, for instance, wearable sensors like wearable pulse oximeters. Thus, in addition to the physiological properties of the patients which have been determined based on the acquired video data, physiological properties of the patients which have been determined based on the sensor signals can be used for allocating the bandwidths for the transmission of the video data from the cameras to the display device. By using these additional sensor-signal-based physiological properties the physiological state of the patients can be captured more completely which can lead to a further improved allocation of the bandwidths and hence to a further improved video surveillance of the patients.

The data transmission system can comprise a) bandwidth request generating units assigned to the cameras, wherein a bandwidth request generating unit assigned to a respective camera is adapted to generate a bandwidth request being indicative of a requested bandwidth or requested change of a bandwidth allocated for a transmission of the video data from the respective camera to the display device depending on the respective determined physiological property, and b) a data transmission system controller for controlling the allocation of the bandwidths depending on the bandwidth requests generated by the bandwidth request generating units. Preferentially, the bandwidth request generating units assigned to the cameras are integrated into the cameras. Moreover, at least one of the person detection unit, the medical procedure information providing unit, the distance information providing unit, the behavior information providing unit, the medical condition information providing unit and the fall information providing unit can comprise subunits fulfilling the respective function for the respective patient, wherein these subunits can be integrated into the respective cameras. For instance, a person detection subunit for detecting a person close to a respective patient can be integrated into the camera surveilling the region in which the respective patient is located. Moreover, the physiological property measuring units can provide their measured physiological properties to the cameras with the integrated bandwidth request generating units. This allows the bandwidth request generating units assigned to the cameras to request a certain bandwidth or a certain increase of the already allocated bandwidth based on these further data.

In a further aspect of the present invention a camera for being used in a hospital video surveillance system as defined in claim 1 is presented, wherein the camera is adapted to surveil a region within a hospital, in which a patient is located, by acquiring video data showing the region, wherein the camera comprises:

a physiological property determination unit for determining a physiological property of the patient based on the acquired video data, wherein the physiological property is a vital sign,     a bandwidth request generating unit for generating a bandwidth request being indicative of a requested bandwidth or requested change of a bandwidth allocated for a transmission of the video data from the camera to a display device of the hospital video surveillance system, wherein the bandwidth request generating unit is adapted to generate the bandwidth request depending on the determined physiological property.

The physiological property determination unit can be adapted to determine for the patient one or several vital signs.

In a further aspect of the present invention a data transmission system controller for being used in a data transmission system of a hospital video surveillance system as defined in claim 1 is presented, wherein the data transmission system controller is adapted to control the data transmission system such that the data transmission system allocates bandwidths for the transmission of the video data from the cameras to the display device depending on the determined physiological properties.

In further aspect of the present invention a hospital video surveillance method is presented, wherein the hospital video surveillance method comprises:
  surveilling several regions within a hospital, in which patients are located, by acquiring video data showing the several regions by using several cameras,
  transmitting the video data from the cameras to the display device by using a data transmission system,
  displaying the video data by using the display device,
  determining physiological properties of the patients based on the acquired video data by a physiological property determination unit, wherein the physiological properties are vital signs,
  allocating bandwidths for the transmission of the video data from the cameras to the display device depending on the determined physiological properties by using the data transmission system.

In a further aspect of the present invention a camera method for surveilling a region within a hospital, in which a patient is located, by acquiring video data showing the region by using a camera as defined in claim 11 is presented, wherein the method comprises:
  determining a physiological property of the patient based on the acquired video data by a physiological property determination unit of the camera, wherein the physiological property is a vital sign,
  generating a bandwidth request being indicative of a requested bandwidth or requested change of a bandwidth allocated for a transmission of the video data from the camera to a display device of a hospital video surveillance system by a bandwidth request generating unit of the camera, wherein the bandwidth request generating unit generates the bandwidth request depending on the determined physiological property.

In a further preferred aspect of the present invention a hospital video surveillance computer program is presented, wherein the computer program comprises program code means for causing the hospital video surveillance system as defined in claim 1 to carry out the hospital video surveillance method as defined in claim 11, when the computer program is run on the hospital video surveillance system.

In another aspect of the present invention a computer program is presented, which comprises program code means for causing the camera as defined in claim 11 to carry out the method as defined in claim 13, when the computer program is run on the camera.

It shall be understood that the hospital video surveillance system of claim 1, the camera of claim 11, the hospital video surveillance method of claim 12, the camera method of claim 13, the hospital video surveillance computer program of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
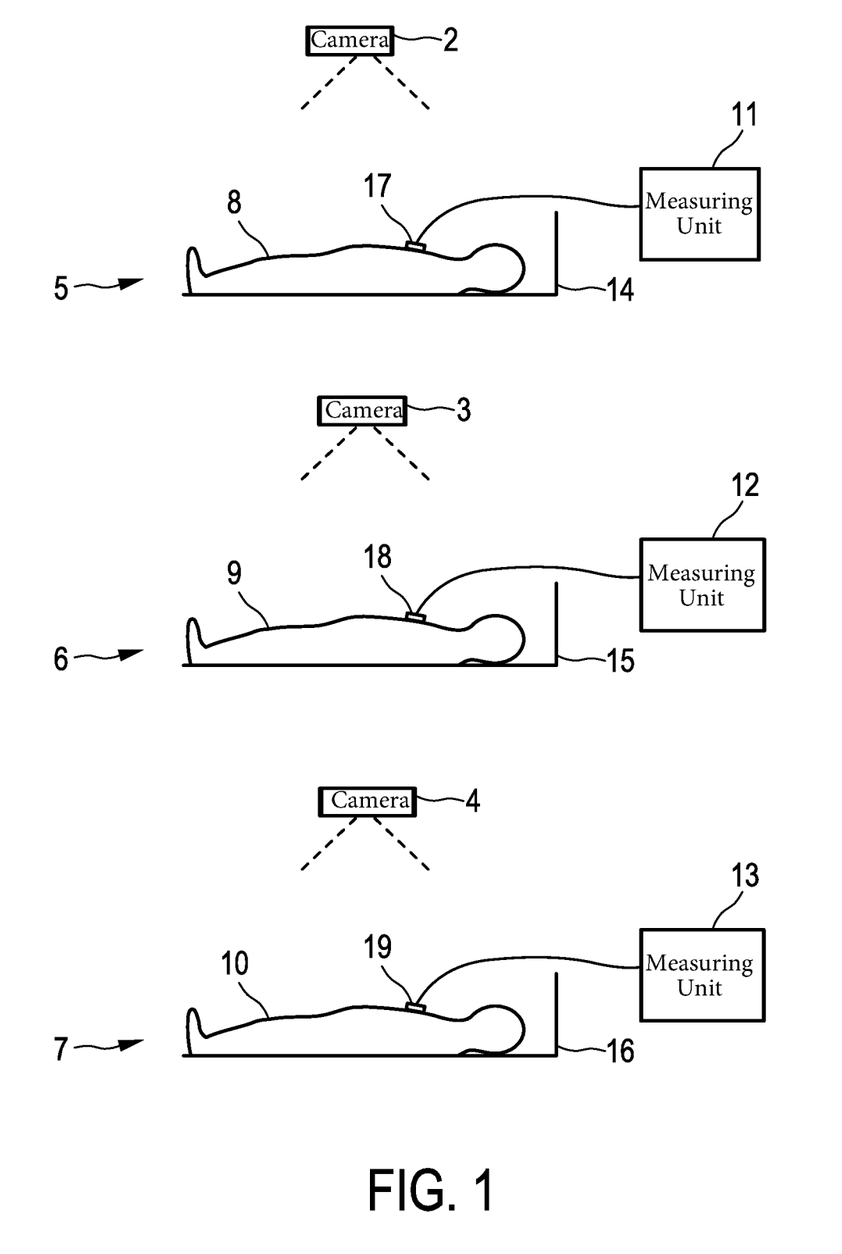
FIG. 1 shows schematically and exemplarily components of an embodiment of a hospital video surveillance system.

FIG. 1 shows schematically and exemplarily components of an embodiment of a hospital video surveillance system comprising several cameras 2, 3, 4 for surveilling several regions 5, 6, 7 within a hospital. In each region 5, 6, 7 a respective patient 8, 9, 10 is located. The cameras 2, 3, 4 are adapted to acquire video data showing the several regions 5, 6, 7. In this embodiment each camera is used for surveilling a region covered by a patient bed 14, 15, 16 in which the respective patient 8, 9, 10 is lying. The patient beds 14, 15, 16 can be situated in a same room or in different rooms.

Figure 2:
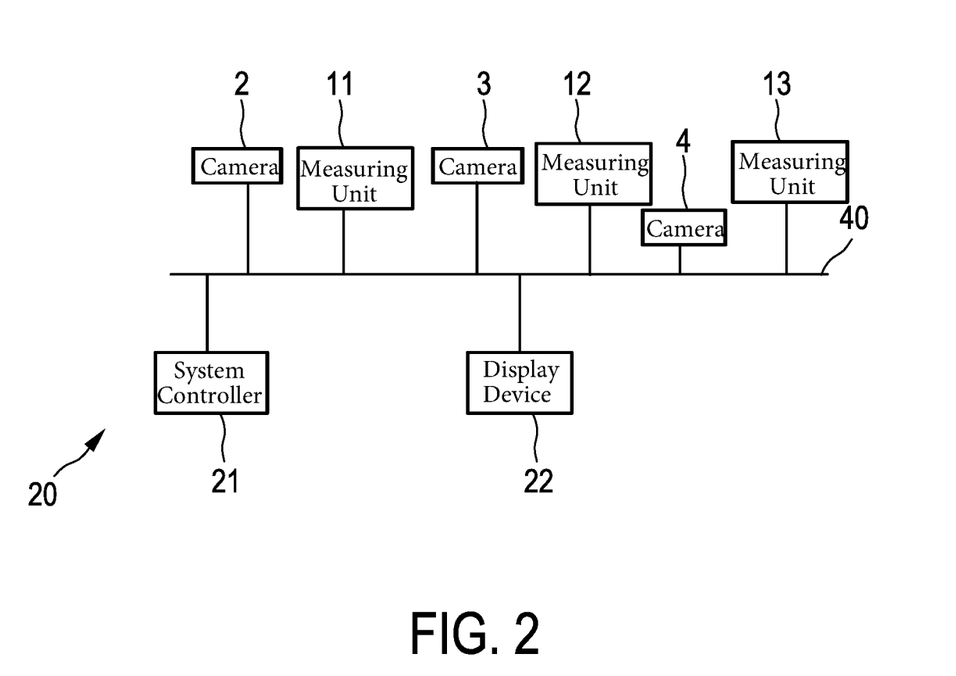
FIG. 2 illustrates schematically and exemplarily a data transmission system of the embodiment of the hospital video surveillance system.

As schematically and exemplarily illustrated in FIG. 2, the hospital video surveillance system further comprises a data transmission system 20 comprising a data connection 40 for transmitting the video data from the cameras 2, 3, 4 to a display device 22. The display device 22 is adapted to display the video data, wherein the display device 22 is preferentially located in a caregivers' room such that a caregiver can monitor the patients via the display device 22 from the caregivers' room.

Figure 3:
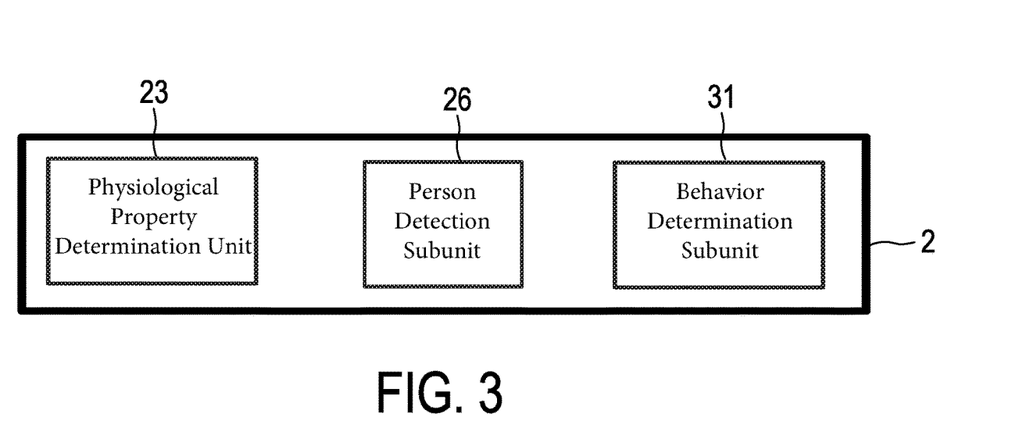
FIG. 3 illustrates schematically and exemplarily a camera of the embodiment of the hospital video surveillance system.

FIG. 3 schematically and exemplarily shows a camera in more detail. In particular, each camera 2, 3, 4 comprises a physiological property determination unit 23 for determining a physiological property of the respective patient 8, 9, 10 based on the acquired video data. In this embodiment the physiological property determination unit 23 is adapted to determine the heart rate and/or the breathing rate of the respective patient based on the acquired video data. For determining the physiological properties known video processing algorithms can be used. For instance, chest motion and/or abdomen motion can be detected in the video data and used for determining the breathing rate and/or other breathing related information. Moreover, remote photoplethysmograhpy technology can be used for determining a pulse signal, the heart rate and other derivate parameters like the heart rate variability (HRV), wherein subtle changes of skin color caused by blood volume changes with every heart beat are detected in the video data. For more details regarding determining physiological properties from video data reference is made to U.S. Pat. No. 9,339,210 B2, U.S. Pat. No. 8,666,116 B2 and U.S. Pat. No. 9,025,826 B2 which are herewith incorporated by reference.

Figure 4:
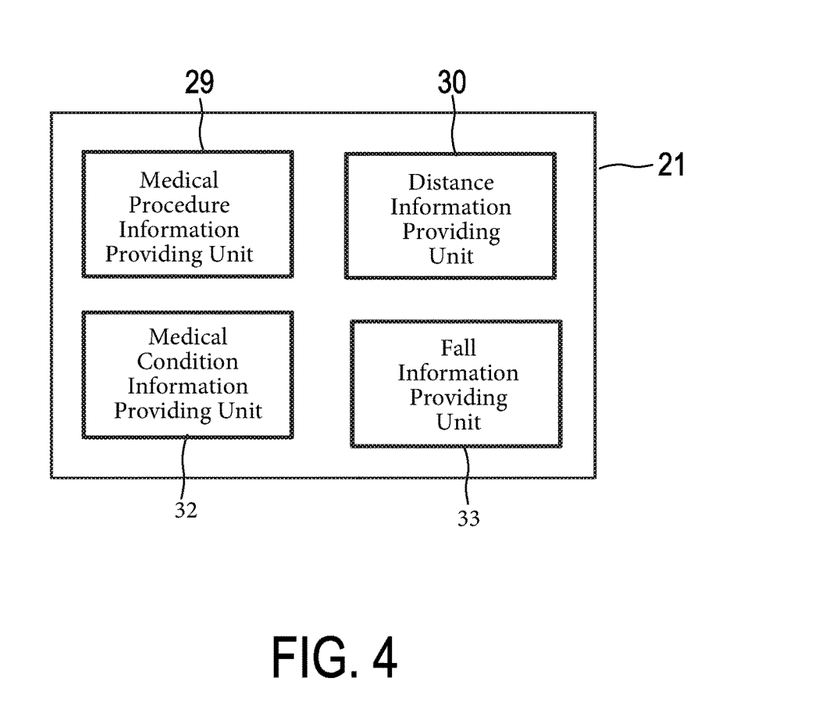
FIG. 4 illustrates schematically and exemplarily a data transmission system controller of the embodiment of the hospital video surveillance system.

The hospital video surveillance system further comprises a data transmission system controller 21 for controlling the data transmission system 20 and particularly for allocating bandwidths for the transmission of the video data from the cameras 2, 3, 4 to the display device 22 depending on the determined physiological properties. The data transmission system controller 21 is preferentially further adapted to allocate the bandwidths for the transmission of the video data depending on the history of the determined physiological properties. Thus, the allocation cannot only be performed based on the current physiological properties of the patient, but also depending on the physiological properties determined in the past. As it is schematically and exemplarily illustrated in FIG. 4, the data transmission system controller 21 comprises a medical procedure information providing unit 29 for providing medical procedure information being indicative of the respective medical procedure the respective patient undergoes, wherein the data transmission system controller 21 is adapted to allocate the bandwidths for the transmission of the video data also depending on the provided medical procedure information. In this embodiment the medical procedure information providing unit 29 is a receiving unit for receiving for each patient the medical procedure information from a patient data server. The data transmission system controller 21 also comprises a medical condition information providing unit 32 for providing medical condition information being indicative of the respective medical condition of the respective patient, for instance, being indicative of the disease the respective patient has. In this embodiment the medical condition information providing unit 32 is a receiving unit for receiving the medical condition information from the patient data server. The data transmission system controller 21 can be adapted to allocate the bandwidths for the transmission of the video data also depending on the provided medical condition information. Moreover, the data transmission system controller 21 comprises a distance information providing unit 30 for providing distance information being indicative of the respective distance of the respective region to the caregivers' room in the hospital. In this embodiment the distance information providing unit 30 is a storing unit in which the distances between the regions and the caregivers' room are stored and from which these distances can be provided. The data transmission system controller 21 is adapted to allocate the bandwidths for the transmission of the video data also depending on the provided distance information.

In this embodiment the video data acquired by the cameras are not only used for being displayed on the display device and for determining the physiological properties of the patients, but they are also used for detecting, besides the patient, a further person within the respective region, wherein this person detection is carried out by a person detection subunit 26. In particular, the person detection subunit 26 is adapted to perform the person detection such that it is determined whether the respective person is a caregiver. In this way it is possible to detect whether a caregiver is close to the respective patient or not. The data transmission system controller 21 is adapted to allocate the bandwidths for the transmission of the video data also depending on this knowledge whether a caregiver is close to the respective patient.

The respective camera also comprises a behavior determination subunit 31 for determining the behavior of the respective patient, especially the respective activity level, wherein the data transmission system controller 21 is adapted to allocate the bandwidths for the transmission of the video data also depending on the determined behaviors. Furthermore, a fall information providing unit 33 is adapted to detect whether the respective patient has fallen out of the respective bed, in order to generate a fall history as fall information. The data transmission system controller 21 is adapted to allocate the bandwidths for the transmission of the video data also depending on this generated and provided fall information.

For determining the fall history known video-based algorithms for the detection of bed exits and bed occupancy can be used. The algorithms can use, for instance, wither motion analysis and/or three-dimensional volume estimation algorithms.

The hospital video surveillance system also comprises physical property measuring units 11, 12, 13 for determining measured physiological properties based on measured sensor signals received from physiological sensors 17, 18, 19 attached to the patients 8, 9, 10. In this embodiment the physiological sensors 17, 18, 19 are wearable sensors for measuring, for instance, the pulse rate, $SpO_2$, et cetera. The data transmission system controller 21 is adapted to allocate the bandwidths for the transmission of the video data also depending on these measured physiological properties. For transmitting these measured physiological properties from the physiological property measuring units 11, 12, 13 to the data transmission system controller 21, the data transmission system 40 can be used.

The data transmission system controller 21 can comprise allocation rules defining the fraction of the overall available bandwidth to be assigned to the transmission of the video data from a certain camera to the display device based on the physiological properties which have been determined based on the acquired video data, the history of these determined physiological properties, whether a caregiver is close to a respective patient, the medical procedure information, the distance information, the behaviors, the medical condition information, the fall information and the physiological properties measured by the physiological property measuring units 11, 12, 13. These allocation rules are predetermined and can be provided by, for instance, a neural network. However, it is of course also possible to provide the allocation rules without using a neural network by defining how the bandwidth should be distributed under which input data situation. The allocation rules can be adapted to assign each patient to one of several patient state classes depending on the determined respective physiological property, to one of several physiological property history classes depending on the respective history of the respective determined physiological property, to one of several medical procedure classes depending on the respective medical procedure information, to one of several behavior classes depending on the respective determined behavior, to one of several medical condition classes depending on the respective provided medical condition information and to one of several fall information classes depending on the respective fall information. The allocation rules can define the distribution of the bandwidths depending on these classes and the information whether a caregiver is close to the respective patient and the distance information.

Figure 5:
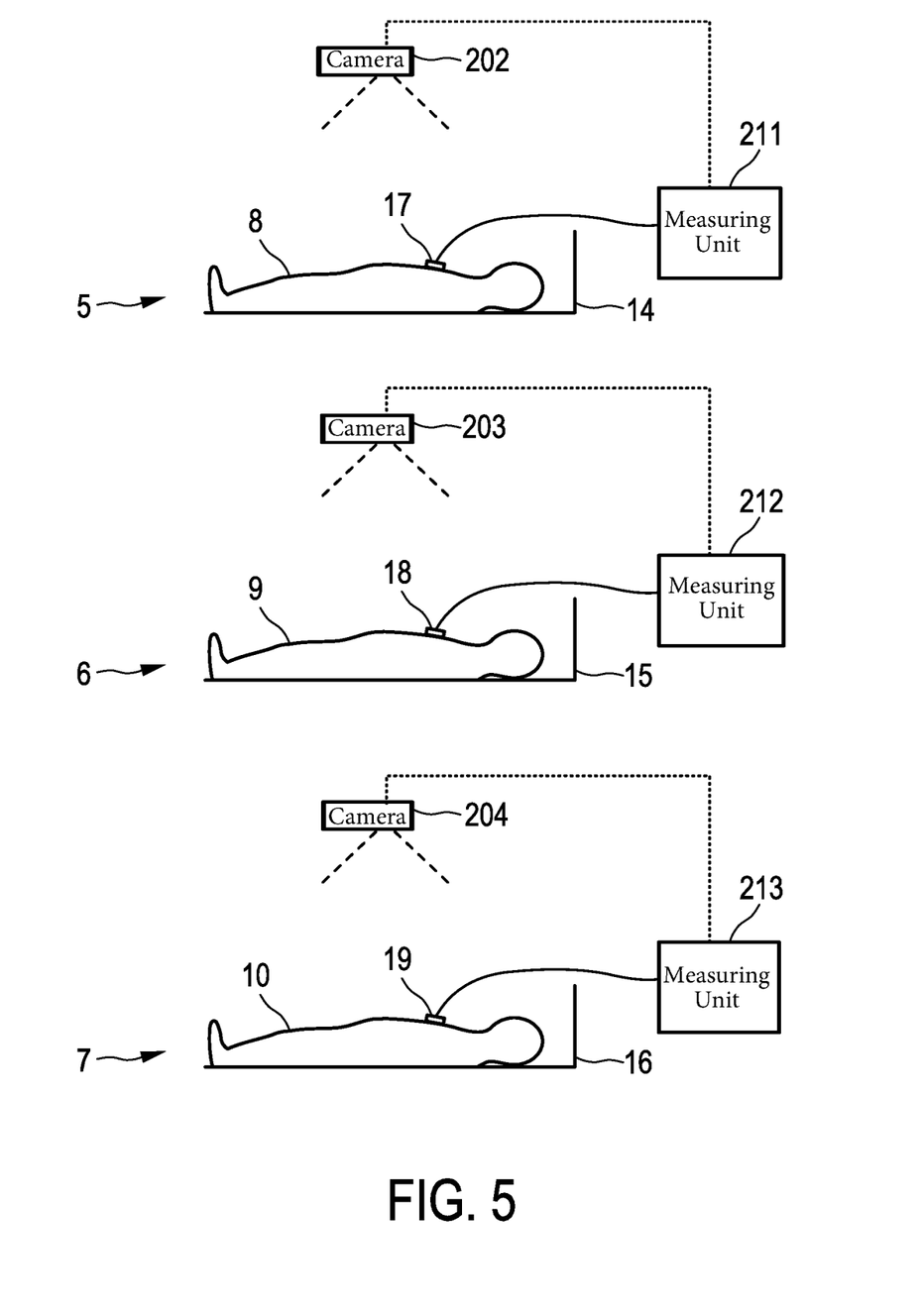
FIG. 5 shows schematically and exemplarily components of a further embodiment of the hospital video surveillance system.
Figure 6:
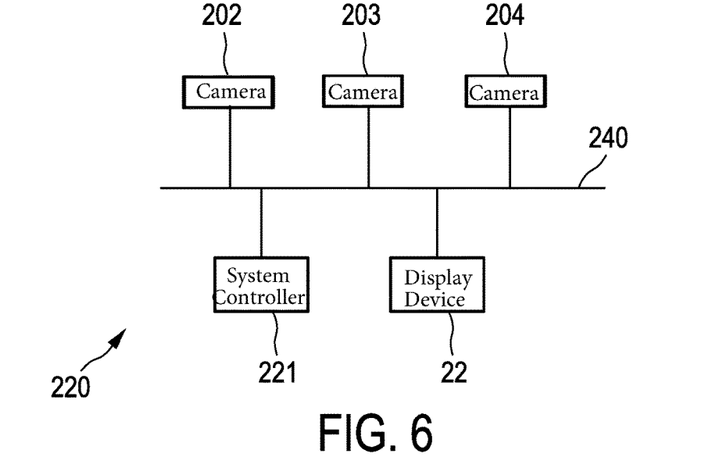
FIG. 6 illustrates schematically and exemplarily components of a data transmission system of the further embodiment of the hospital video surveillance system.
Figure 7:
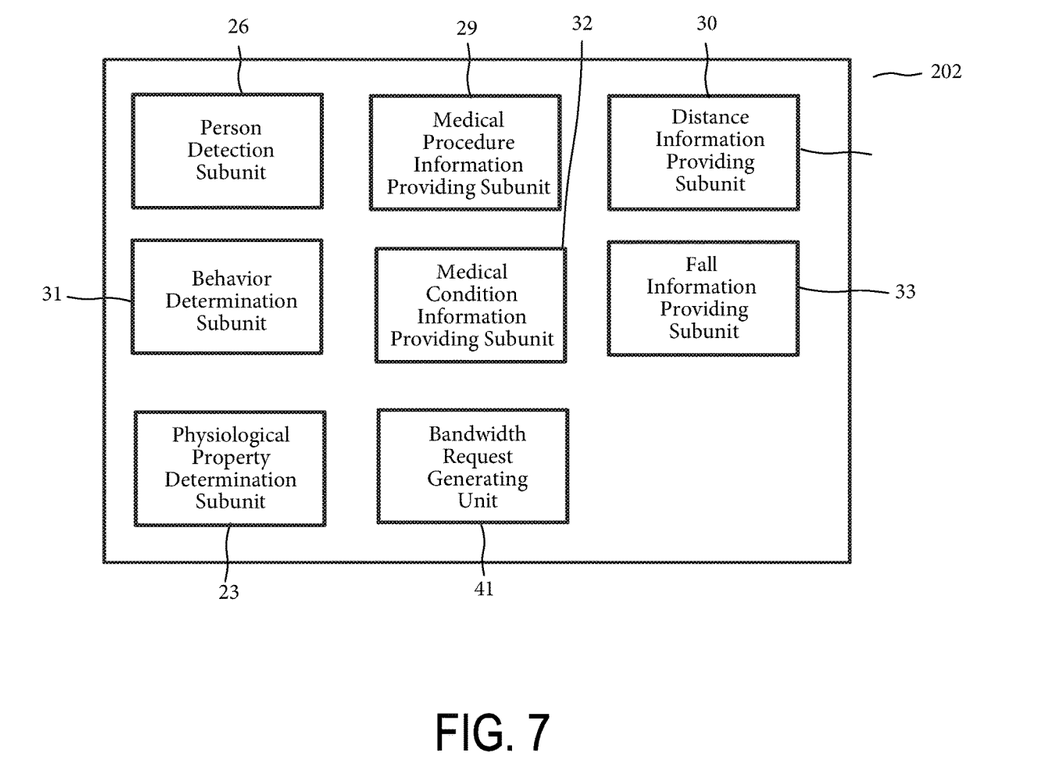
FIG. 7 illustrates schematically and exemplarily a camera of the further embodiment of the hospital video surveillance system.

FIG. 5 shows schematically and exemplarily a further embodiment of the hospital video surveillance system. In this embodiment several cameras 202, 203, 204 are used for surveilling several regions 5, 6, 7 within a hospital, in which patients 8, 9, 10 are located, by acquiring video data showing the several regions 5, 6, 7. FIG. 6 schematically and exemplarily illustrates components of the data transmission system 220 of the hospital video surveillance system. The data transmission system 220 comprises a data connection 240 to which the cameras 202, 203, 204 are connected. Also a display device 22 for displaying the video data is connected to the data connection 240. The data transmission system 220 further comprises a data transmission system controller 221 for controlling the data transmission system. As schematically and exemplarily illustrated in FIG. 7, the camera 202 and also the other cameras 203, 204 comprise the physiological property determination subunit 23 for determining a physiological property of the respective patient based on the acquired video data, the person detection subunit 26, a medical procedure information providing subunit 29, a distance information providing subunit 30, the behavior determination subunit 31, a medical condition information providing subunit 32 and a fall information providing subunit 33. Moreover, the cameras 202, 203, 204 are connected with physiological property measuring units 211, 212, 213 for determining measured physiological properties based on measured sensor signals received from the physiological sensors 17, 18, 19 attached to the patients 8, 9, 10. In addition, each camera comprises a bandwidth request generating unit 41 for generating a bandwidth request being indicative of a requested bandwidth or requested change of a bandwidth allocated for a transmission of the video data from a respective camera to the display device depending on the determined physiological property and the further provided input data like the information whether a caregiver is close to the respective patient, the medical procedure information, the distance information, the determined behavior of the respective patient, the medical condition information, the fall information and the measured physiological properties received from the physiological property measuring units 211, 212, 213. The requests are handled by the data transmission system controller 221 which is adapted to control the allocation of the bandwidths depending on the bandwidth requests generated by and received from the bandwidth request generating units 41. For generating the requests request generating rules can be provided, which define the generation of the bandwidth requests depending on the input data. Moreover, request handling rules can be provided, which define the allocation of the bandwidths depending on the generated bandwidth requests.

The bandwidth request generating units 41 can also be regarded as being components of the data transmission system 220, because the generated bandwidth requests are used for determining the distribution of the bandwidths within the data transmission system 220. The data transmission system 220 can therefore be regarded as comprising the data connection 240, the data transmission system controller 221 and the bandwidth request generating units 41.

Figure 8:
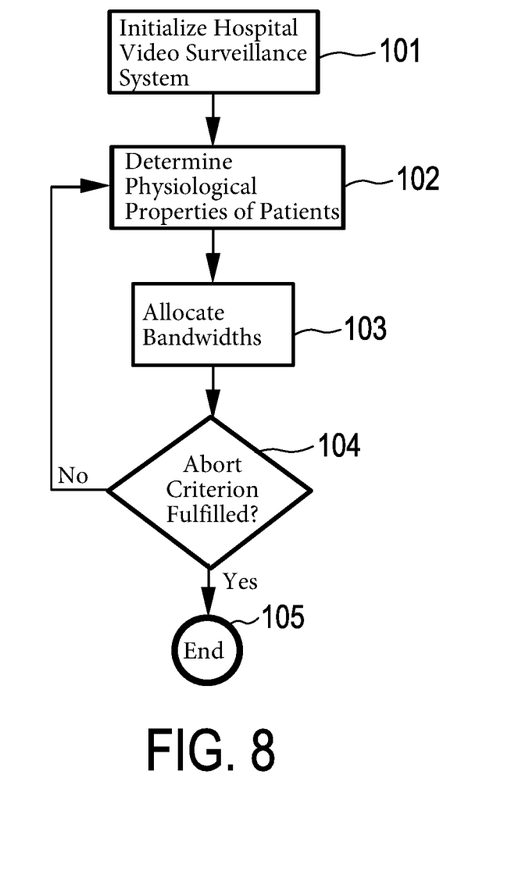
FIG. 8 shows a flowchart exemplarily illustrating an embodiment of a hospital video surveillance method.

In the following an embodiment of a hospital video surveillance method will exemplarily be described with reference to a flowchart shown in FIG. 8.

In step 101 the hospital video surveillance system is started and initialized, wherein at the beginning the bandwidth is equally distributed and relative low for each camera. Thus, after the hospital video surveillance method has been started, the regions within the hospital are surveilled by acquiring video data, the video data are transmitted from the cameras to the display device by using the data transmission system with equally distributed, relatively low bandwidths and the video data are shown on the display device. While this video surveillance is maintained, in step 102 the physiological properties of the patients are determined based on the acquired video data by the physiological property determination subunits. Optionally, in step 102 further data can be provided like data indicating whether a caregiver is close to a respective patient, the medical procedure information, the distance information, the behavior of the respective patient, the medical condition information, the fall information and/or the measured respective physiological property provided by the respective physiological property measuring unit.

In step 103 the bandwidths distribution for the transmission of the video data from the cameras to the display device is changed or remains the same, wherein whether the bandwidths distribution is changed or remains and, if changed, how the bandwidths distribution is changed is determined depending on the determined physiological properties. Thus, in step 103 the determined physiological properties are used for the bandwidths allocation. For instance, the cameras can generate bandwidth requests depending on the physiological properties and the data transmission system controller can allocate the bandwidths depending on the generated bandwidths requests, or the data transmission system controller can allocate the bandwidths directly depending on the physiological properties. Moreover, in step 103 optionally also the further data provided in step 102 can be used for allocating the bandwidths. Hence, the video surveillance of the regions, in which the patients are located, is maintained, while the distribution of the bandwidths can be modified in step 103.

In step 104 it is checked whether an abort criterion is fulfilled. If this is the case, the hospital video surveillance method ends in step 105. Otherwise the method continues with step 102. The abort criterion is, for instance, whether a user has input via an input device like a button, a keyboard, a computer mouse, a touch pad, et cetera that the hospital video surveillance method should be stopped. If this method should not be stopped, steps 102 and 103 can be carried out in a loop, in order to allow the hospital video surveillance method to adapt the video surveillance dynamically to the current situation.

The determination of a physiological property by the physiological property determination unit of the camera and the generation of the bandwidth requests by the bandwidth request generating unit of the camera as described above with respect to steps 102 and 103 can be regarded as being steps of a camera method for surveilling a region within a hospital, in which a patient is located.

Continuous video surveillance of patients can provide an easy and fast detection of dangerous situations like attempts to leave a bed without assistance and allows for a context-based interpretation of physiological properties, especially of vital signs. However, a continuous video surveillance of patients and broadcasting across especially large hospitals requires a sufficiently large network bandwidth which might not be present.

The cameras can be used for monitoring the patient's physiological state and behavior including activity and for automatically registering attempts of bed exits. The cameras are preferentially located over each patient bed in the hospital such that the video streaming, which is preferentially a continuous video streaming, requires a relatively high bandwidth and might also require a sophisticated quality of service (QoS) system. In order to cope with the bandwidth issue, the quality of video streaming can be significantly reduced, but this can jeopardize the practical value of the camera-based monitoring. The above described hospital video surveillance system and method provide therefore valuable information about changes in, for instance, a physiological state of a patient without latency such that this information can be used for controlling the allocation of the limited bandwidth. In particular, the network bandwidth can be adaptively assigned and reassigned in the video surveillance infrastructure depending on the physiological state of the respective patient, a detection of a specific dangerous activity like an attempt to leave the patient bed, et cetera. The data transmission system controller can be adapted to allocate a higher bandwidth to a video stream from a certain patient, if, for instance, detected vital signs suddenly change or an attempt to leave a patient bed is registered, in order to allow higher frame rates and an improved visual quality. Thus, an adaptive distribution of the bandwidths and therefore of the video quality can be achieved based on real context information like vital signs information, activity information, et cetera rather than on visual quality or other aspects not related to, for instance, a health condition of a monitored person.

The cameras can use the Vital Signs Camera technology of the company Philips. However, also other technologies can be used. The cameras are preferentially adapted to continuously measure vital body signs of the respective patient as physiological properties and to determine the respective patient's body activity as behavior by means of video processing at the respective camera. In an embodiment in a default mode, which might be present immediately after the hospital video surveillance system has been activated, the frame rate and the bit rate allocated to the video streams from the cameras can be relatively low. The allocation rules might define that, as soon as changes in the measured vital signs exceed a certain predefined threshold for a respective patient or an activity is detected, which might lead to a bed exit, a higher bandwidth is requested and assigned to the corresponding camera such that an improved quality and frame rate of the surveillance video of that patient is automatically provided. In addition, vital signs, the activity, et cetera can be measured by means of wearable sensors. For instance, for detecting the activity of a patient, an accelerometer-based wearable sensor might be used and for measuring a pulse rate and/or SpO$_2$ values a wearable pulse oximeter might be used. The allocation rules can define that, if a patient becomes active and/or the pulse rate changes by more than a predefined threshold and/or the SpO$_2$ values change by more than a predefined threshold, a higher bandwidth is requested and allocated to the respective camera, in order to provide an improved quality of video streaming. Moreover, the allocation rules can define that a relatively low bandwidth is automatically allocated to a camera which has registered the presence of a caregiver in the respective patient room, because a remote surveillance is not needed then. The bandwidth of video streaming can also be allocated depending on, as indicated above, the diagnosis of a patient, fall information, which might be regarded as being indicative of a fall probability, a medical procedure including a medical workflow assigned to a respective patient, et cetera. As also indicated above, the bandwidth of video streaming can also be allocated depending on, for instance, the location of the respective patient room relative to the caregivers' room which might be a nurse station. A higher bandwidth should be assigned to a patient room located further from the caregivers' room.

Although in above described embodiments the fall information is fall history information being indicative of the fall history of the respective patient, the fall information can also be a fall risk score which is calculated based on at least one of a) past one or several physiological properties and/or b) current one or several physiological properties.

Although in above described embodiments a relatively large group of input data has been used for distributing the bandwidths among the cameras, in other embodiments only one or some of these input data may be used for distributing the bandwidths among the cameras.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of the physiological properties of the patients based on the acquired video data, the detection of a person within the respective region, the provision of information like medical procedure information, distance information, et cetera, the determination of the behaviors of the patients, et cetera performed by one or several units or devices can be performed by any other number of units or devices. These operations and/or the control of the hospital video surveillance system in accordance with the hospital video surveillance method and/or the control of a camera of the hospital video surveillance system in accordance with the camera method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a hospital video surveillance system comprising several cameras for acquiring video data for surveilling several patient regions. The video data are transmitted from the cameras to a display device and are used to determine physiological properties of patients, wherein the bandwidths for the transmission of the video data are allocated depending on the determined physiological properties. Thus, the bandwidth allocation considers the physiological states of the patients, which can ensure that a sufficient bandwidth is provided where it is really required. This is especially useful, if the overall bandwidth is limited. Moreover, since the video data are used for fulfilling several functions, i.e. surveilling the several patient regions and determining the physiological properties, the overall system can be very compact and less or no additional physiological sensors might be required.

The invention claimed is:

1. A hospital video surveillance system comprising:
   several cameras configured to acquire video showing several regions within a hospital in which patients are located;
   a display device configured to display the video data;
   a data transmission system configured to transmit the video data from the several cameras to the display device; and
   a physiological property determination unit configured to determine physiological properties of the patients based on the acquired video data, wherein the physiological properties are vital signs and the data transmission system is further configured to allocate bandwidths for the transmission of the video data from the several cameras to the display device depending on the determined physiological properties and allocate a larger bandwidth after a fall risk score is larger than a fall risk threshold.

2. The hospital video surveillance system as defined in claim 1, wherein the data transmission system is further configured to allocate the bandwidths for the transmission of the video data depending on a history of the determined physiological properties.

3. The hospital video surveillance system as defined in claim 1, wherein the hospital video surveillance system further comprises:
   a person detection unit configured to detect, besides the patient, a further person within the respective region, wherein the data transmission system is further configured to allocate the bandwidths for the transmission of the video data depending on the detection of the further person.

4. The hospital video surveillance system as defined in claim 1, wherein the hospital video surveillance system further comprises:
   a medical procedure information providing unit configured to provide medical procedure information being indicative of the respective medical procedure the respective patient undergoes, wherein the data transmission system is further configured to allocate the bandwidths for the transmission of the video data depending on the provided medical procedure information.

5. The hospital video surveillance system as defined in claim 1, wherein the hospital video surveillance system further comprises:
   a distance information providing unit configured to provide distance information being indicative of the respective distance of the respective region to a caregivers' room in the hospital, wherein the data transmission system is further configured to allocate the bandwidths for the transmission of the video data depending on the provided distance information.

6. The hospital video surveillance system as defined in claim 1, wherein the hospital video surveillance system further comprises:
   a behavior information providing unit configured to provide behavior information being indicative of the behavior of the respective patient, wherein the data transmission system is further configured to allocate the bandwidths for the transmission of the video data depending on the provided respective behavior information.

7. The hospital video surveillance system as defined in claim 1, wherein the hospital video surveillance system further comprises:
   a medical condition information providing unit configured to provide medical condition information being indicative of the respective medical condition of the respective patient, wherein the data transmission system is further configured to allocate the bandwidths for the transmission of the video data depending on the provided respective medical condition information.

8. The hospital video surveillance system as defined in claim 1, wherein the hospital video surveillance system further comprises:
   a fall information providing unit configured to provide fall information being indicative of the respective fall history and/or of the respective fall risk of the respective patient, wherein the data transmission system is further configured to allocate the bandwidths for the transmission of the video data depending on the provided respective fall information.

9. The hospital video surveillance system as defined in claim 1, wherein the data transmission system further comprises:
   bandwidth request generating units assigned to the several cameras, wherein a bandwidth request generating unit assigned to a respective camera is configured to generate a bandwidth request being indicative of a requested bandwidth or requested change of a bandwidth allocated for a transmission of the video data from the respective camera to the display device depending on the determined respective physiological property,
   a data transmission system controller configured to control the allocation of the bandwidths depending on the bandwidth requests generated by the bandwidth request generating units.

10. A camera used in the hospital video surveillance system as defined in claim 1, wherein the camera is configured to surveil a region within a hospital, in which a patient is located, by acquiring video data showing the region, wherein the camera further comprises:
    a physiological property determination unit configured to determine a physiological property of the patient based on the acquired video data, wherein the physiological property is a vital sign; and
    a bandwidth request generating unit configured to generate a bandwidth request depending on the determined physiological property indicative of a requested bandwidth or requested change of a bandwidth allocated for a transmission of the video data from the camera to a display device of the hospital video surveillance system.

11. A data transmission system controller used in the data transmission system of the hospital video surveillance system as defined in claim 1, wherein the data transmission system controller is configured to control the data transmission system such that the data transmission system allocates bandwidths for the transmission of the video data from the cameras to the display device depending on the determined physiological properties.

12. A hospital video surveillance method comprising:
    surveilling several regions within a hospital, in which patients are located, by acquiring video data showing the several regions by using several cameras;
    transmitting the video data from the several cameras to the display device by using a data transmission system;
    displaying the video data by using the display device;

determining physiological properties of the patients based on the acquired video data by a physiological property determination unit, wherein the physiological properties are vital signs;

allocating bandwidths for the transmission of the video data from the several cameras to the display device depending on the determined physiological properties by using the data transmission system; and allocating a larger bandwidth after a fall risk score is larger than a fall risk threshold.

13. The hospital video surveillance method of claim 12, further comprising:

generating a bandwidth request depending on the determined physiological property indicative of a requested bandwidth or requested change of a bandwidth allocated for a transmission of the video data from a respective camera of the several cameras to a display device of a hospital video surveillance system by a bandwidth request generating unit of the respective camera.

14. A non-transitory computer-readable medium having instructions stored thereon for causing a hospital video surveillance system to carry out a hospital video surveillance method, the non-transitory medium comprising:

instructions for surveilling several regions within a hospital, in which patients are located, by acquiring video data showing the several regions by using several cameras;

instructions for transmitting the video data from the several cameras to the display device by using a data transmission system;

instructions for displaying the video data by using the display device;

instructions for determining physiological properties of the patients based on the acquired video data by a physiological property determination unit, wherein the physiological properties are vital signs;

instructions for allocating bandwidths for the transmission of the video data from the several cameras to the display device depending on the determined physiological properties by using the data transmission system; and instructions for allocating a larger bandwidth after a fall risk score is larger than a fall risk threshold.

15. The non-transitory computer-readable medium of claim 14, wherein the non-transitory computer-readable medium is located within a camera.

* * * * *